United States Patent [19]

Lormeau et al.

[11] Patent Number: 4,788,307

[45] Date of Patent: Nov. 29, 1988

[54] OLIGOSACCHARIDIC FRACTIONS DEVOID OR PRACTICALLY DEVOID OF ANTITHROMBOTIC ACTIVITY

[75] Inventors: Jean-Claude Lormeau, Maromme; Jean Choay, Paris, both of France

[73] Assignee: Choay S.A., Paris, France

[21] Appl. No.: 8,631

[22] Filed: Jan. 29, 1987

Related U.S. Application Data

[63] Continuation-in-part of Ser. No. 681,017, Dec. 13, 1984, Pat. No. 4,686,288.

[51] Int. Cl.$^4$ .................. A61K 31/725; C08B 37/10; C07H 1/00
[52] U.S. Cl. ...................... 536/21; 536/123; 536/124; 514/56; 514/822
[58] Field of Search ............ 536/21, 123, 124; 514/56, 822

[56] References Cited

U.S. PATENT DOCUMENTS

| | | | |
|---|---|---|---|
| 4,175,182 | 11/1979 | Schmer | 536/21 |
| 4,281,108 | 7/1981 | Fussi | 536/21 |
| 4,474,770 | 10/1984 | Lormeau et al. | 536/21 |
| 4,486,420 | 12/1984 | Lormeau et al. | 536/21 |
| 4,496,550 | 1/1985 | Lindahl et al. | 536/21 |
| 4,500,519 | 2/1985 | Lormeau et al. | 536/21 |
| 4,686,288 | 8/1987 | Lormeau et al. | 536/21 |

FOREIGN PATENT DOCUMENTS 2071127 9/1981 United Kingdom ............ 536/21

*Primary Examiner*—Ronald W. Griffin
*Attorney, Agent, or Firm*—Weiser & Stapler

[57] ABSTRACT

The oligosaccharidic fractions of the invention are soluble in an hydro-alcoholic mixture 50/50 (v/v) in which is added 0.5% NaCl, at pH 3.8, are constituted by chains the majority of which have 2 to 14 sugar units, are terminated by end units with a 2,5-anhydromanno structure and are devoid or practically devoid of anti-thrombotic activity.

12 Claims, 1 Drawing Sheet

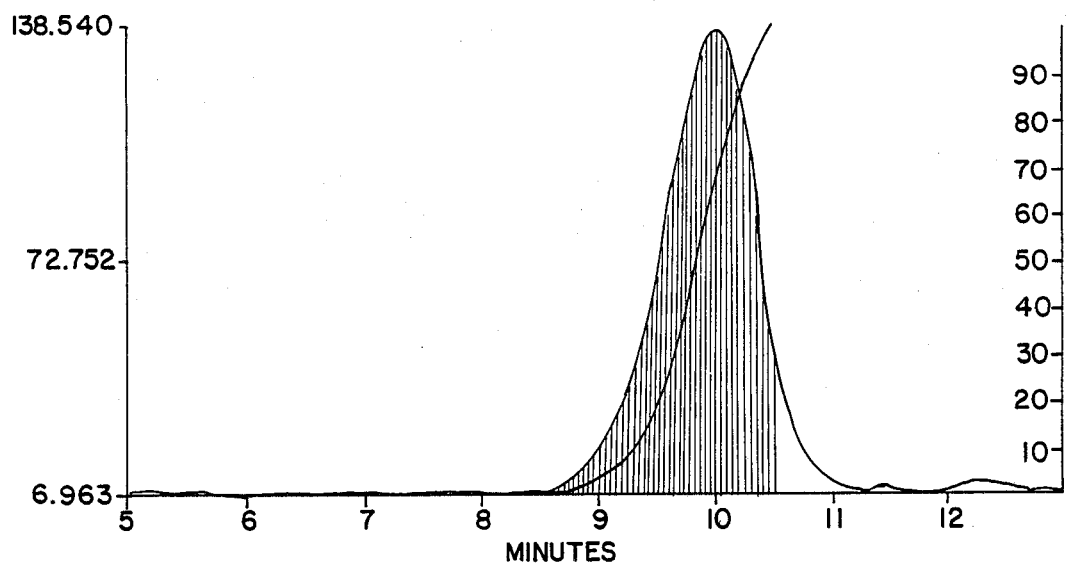
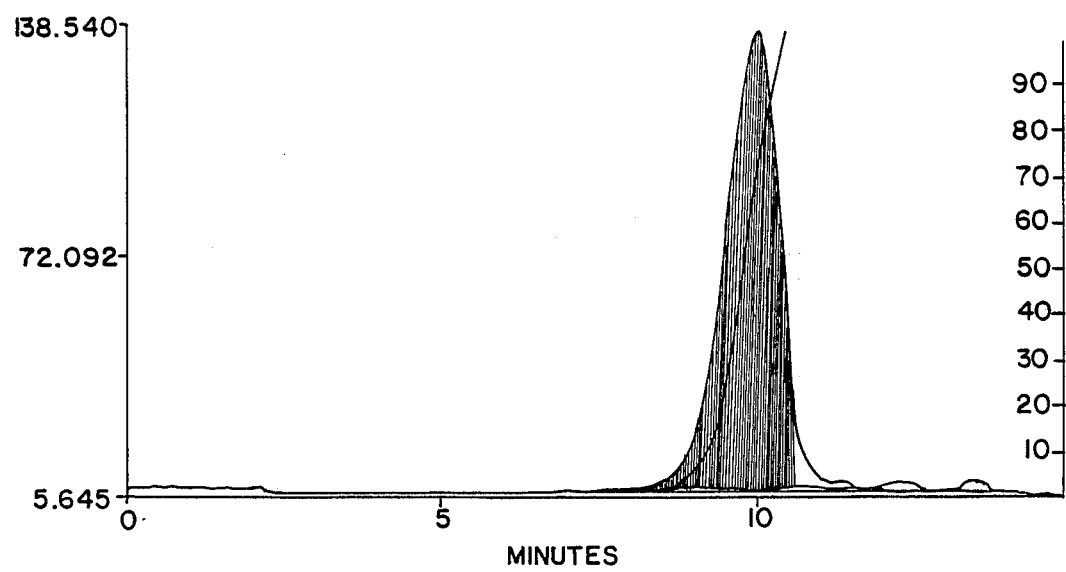

OLIGOSACCHARIDIC FRACTIONS DEVOID OR PRACTICALLY DEVOID OF ANTITHROMBOTIC ACTIVITY

The invention is a c.i.p. of U.S. patent application Ser. No. 681,017 of Dec. 13, 1984, now U.S. Pat. No. 4,686,288, issued Aug. 11, 1987, which relates to a process for preparing mucopolysaccharide compositions endowed with high antithrombotic activity.

It is known that compositions of this type have been obtained from heparin by alcoholic extraction, or again, by depolymerization by chemical or enzymatical route.

In general, these processes enable the production of compositions or fractions consisting of mucopolysaccharides or MPS whose chains contain about 25 to 30 units at the most and possess an anti-Xa activity measured by the Yin Wessler titer (YW) higher than that of heparin and an overall anti-coagulant activity, expressed by the USP titer, less than that of heparin, this titer can even have a value which is from very low to practically nil.

These products have the interest of exerting a more specific activity than heparin on certain steps brought into play in the coagulation process.

In a given treatment, the product is chosen with regard to its YW titer and YW/USP ratio. In that respect the inventors have studied means enabling the easy production of compositions corresponding to a given profile as regards, in particular, their YW titer and their ratio of YW to USP titers, applicants have observed that by operating under particular conditions, it is possible to isolate such products from other MPS compositions.

According to said U.S. patent application there is provided a process characterized in that MPS compositions formed from a majority of MPS chains of molecular weight (MW) of about 1800 to 8000 daltons, having a YW titer and a ratio of YW/USP titers higher than that of heparin are subjected to at least one fractionation step, in order to separate selectively from said compositions at least the major part of chains having MW lower than about 2000 and those having a higher MW but a sulfate content lower than the sulfate average content of the mixture chain and that the fractions freed from said chains are recovered. These chains show a ratio of YW to USP titer smaller than the one of the starting compositions but higher than the one of heparin, with a USP titer higher than that of the starting compositions.

Preferably, the fractionation step is carried out by means of a mixture 50/50 (v/v) of (1) water containing about 0,5% of an inorganic salt and (2) an organic solvent, this solvent being selected from among those in which at least a majority of the products sought is selectively insoluble and precipitates.

The relative proportions of inorganic salt and of solvent are adjusted and this according to the pH of the medium to obtain the desired precipitation of the MPS chains.

According to a preferred feature, the organic solvent is advantageously an alcoholic solvent, more especially ethanol.

According to another preferred feature, the organic salt used is constituted, particularly, by the sodium or potassium chloride or any other salt miscible in the organic solvent used.

According to another preferred feature, the pH of the reaction mixture is adjusted to a value corresponding to an acid pH, more especially to a pH less than 4, particularly of 3–8. According to a preferred embodiment of said invention, the MPS compositions employed for the fractionation contain a majority of chains of MW in the range of about 1800 to 8000, possessing a ratio of the YW to USP titers of at least about 10 and a YW titer of about 200 to 250 $\mu$/mg. The Yin-Wessler titer is used for measuring the anti-Xa activity according to Yin et al. in J. Lab. Clin. Med. 1973, 81, p. 298. The U.S.P. titer enables the measurement of the overall anticoagulant activity.

The U.S.P. test is described in "Pharmacopea of the U.S. of America", XIX, pages 229–230 (see also the second supplement USP-NF, page 62, and the fourth supplement USP, page 90, respectively entitled "Drug substances" and "Dosage forms".

These compositions are advantageously obtained by a partial depolymerisation process of heparin under the action of chemical agents such as nitrous acid. Recourse is had particularly to the process described by applicants in the second application for a certificate of addition No. 80.06282 of 20/03/1980 to Pat. FR No. 78.31357 of 6/11/1978. Advantageously, le depolymerisation process which is performed is based on self-regulation of the depolymerisation reaction such as described in patent application FR No. 81.07283 of 10/04/1981 in the name of applicants.

According to the most general aspect of this autoregulated depolymerisation, heparin is reacted with nitrous acid in an aqueous medium at a pH of about 2 to 3, advantageously of 2.5, in amounts such that heparin concentration is of at least about 8% in weight and nitrous acid molarity of about 0.02M to 0.1M.

When the depolymerisation reaction stops by itself, after having consumed all the nitrous acid, the MPS mixture of the kind of those which can be precipitated by an organic solvent is recovered.

Nitrous acid is generated in situ by adding an acid having advantageously biologically acceptable anions, such as HCl or $CH_3COOH$, to a nitrous acid derivative, particularly a salt, an ether-salt and more especially amn alkaline or an alkaline-earth salt. $NaNO_2$ is more particularly used at a molarity of 0.03 to 0.05M.

Said process is preferably performed with a $NaNO_2$ molarity of 0.040M to 0.046M more particularly of about 0.043M.

Preferably, the MPS compositions employed possess at the reducing end, a unit of 2,5 anhydromanno structure, preferably selected from among 2,5-anhydromannoic acid groups or 2,5-anhydromannitol.

The starting MPS compositions corresponding to the characteristics of YW and USP titers given above are placed in solution in a proportion of 5% w/v in water containing 10 g/l of NaCl.

After adjustment of the pH to 3.8, the fractionation of these MPS is carried out by means of an organic solvent enabling the selective precipitation of the MPS chains possessing the highest molecular weights and/or the most sulfated of the mixture.

Preferably, the organic solvent is an alcoholic solvent, more especially ethanol.

While the chains with low MW and the lowest sulphate content stay in solution and are thus separated, the precipitated fraction as well as the solubilized fraction can be recovered in further steps.

The MPS compositions which precipitate, are characterized in that they are essentially formed of chains (1) of an average molecular weight of 4000 to 5000 daltons, particularly about 4500 (2) possessing a YW titer of about 180 to 200 μ/mg and a ratio of the YW-/USP titers, less than 10, particularly of about 6 to 3 more especially of about 4. Said compositions are formed of a majority of chains which are terminated by units of 2,5-anhydromanno structure when the starting compositions are obtained by a nitrous heparin depolymerisation process.

Said precipitated compositions obtained according to said process are endowed with biological activities enabling them in particular to control specifically certain steps of blood clotting. These compositions are hence particularly valuable for developing medicaments which can be used, particularly, for the prevention of thrombosis and aging of the tissues.

The present invention more particularly relates to the soluble fractions such as those obtained when carrying out the above described process. They consist of a mixture of heparinic oligosaccharides having the following features:

they are soluble in an hydro-alcoholic mixture 50/50 v/v in which is added 0,5% NaCl, at pH 3.8, they are constituted by chains the majority of which have 2 to 14 sugar units and are end terminated by units having a 2,5 anhydromanno structure which results from the method for the obtention thereof, their HPLC profile is characterized by the following figures: weight average about 2430; number average about 1980; peak molecular weight about 1850, they are devoid or practically devoid of anticoagulant activity as expressed by the USP method and have a low anti-Xa activity as measured by the Yin and Wessler method.

As the depolymerization step is advantageously followed by an hydrogenation step to reduce the 2,5-anhydromannose end terminal units into 2,5-anhydromannitol groups, the soluble fractions have such an end unit.

In a further step said oligosaccharides can be fractionned according to their molecular weight by gel filtrating the soluble fraction.

In another further step the different molecular weight fractions can be separated, by using an exchange ion chromatography, in different kinds of oligosaccharides according to their charge density.

The recovery of the oligosaccharides after said fractionation steps is advantageously performed by alcoholic precipitation for example and lyophilisation. Particularly advantageous oligosaccharides consist in mixtures of hexa and octasaccharides, more particularly in hexasaccharides. Such oligosaccharides have a high activity on the inhibition of neoangeiogenesis. They are useful as active principle of drugs in association with a pharmaceutical carrier.

Said medicaments are used under the usual administration forms and doses for a given indication.

The soluble fractions and oligosaccharides are also useful as starting materials to obtain oligosaccharides able to bind to FGF (fibroblast growth factor) and ECGF (endothelial cell growth factor). Such a use is of great importance as the inventors have found that the oligosaccharides having a high affinity for growth factors have an activity on cellular division and differentiation and are useful inter alia to stimulate cell regeneration. Said growth factors-affine oligosaccharides are the subject matter of FR patent application No. 86/05546 filed on Apr. 17, 1986, in the name of SANOFI.

The soluble fractions obtained according to the invention are useful for the constitution of biological reagents useful in the laboratory, particularly as a comparison reference for the study of other products of which the anticoagulant activity is tested, particularly at the level of inhibition of the Xa factor.

Other characteristics and advantages of the invention will appear in the examples which follow with reference to the FIGURE which represents HPLC curves of a soluble fraction such as obtained by carrying out said fractionation process.

EXAMPLE 1

Process for obtaining MPS compositions practically devoid of antithrombotic activity.

500 g of injectable heparin, in the form of sodium salt, are placed in solution in 4500 ml of demineralized water, at a temperature of 18° C.

The YW/USP ratio of the heparin used is in the vicinity of 1, these titers having a value of the order of 160-170.

The solution obtained is subjected to vigorous stirring, and its pH is lowered to 2.5 by the addition of concentrated hydrochloric acid. Then 15 g of sodium nitrite dissolved in 300 ml of water are added. The pH of the reaction is adjusted to 2.5 by concentrated hydrochloric acid, and the total value of the solution is brought to 5000 ml. The reaction is left to take place for 45 minutes and then the absence of residual nitrous ions in the reaction solution is checked, by means of indicator paper impregnated with starch potassium iodide (development of a blue-violet colour in the presence of $NO_2^-$ ions).

The reation is allowed to continue up to the total disappearance of nitrous ions and the absence of reaction with iodo-starch paper, by carrying out checks every 3 or 4 minutes.

When these checks become negative, the reaction is considered as having been completed.

The pH of the solution is then raised to 10 by means of concentrated soda, and 5 g of sodium-tetrahydrideborate is added.

The solution is kept under stirring for 15 hours.

The unreacted sodium tetrahydrideborate is destroyed by lowering the pH to 3 by means of concentrated hydrochloric acid. The solution is subjected to sitrring for 15 minutes, then the pH is readjusted to 7.0 by means of concentrated soda.

MPS compositions endowed with an antithrombotic acitivity are recovered by the addition of 10 l of ethanol. After 48 hours standing, the product is decanted and the supernatant liquor recovered for further processing.

The precipitate is redissolved in 9 liters of dimineralized water. 100 g of sodium chloride are added, and the pH of the solution is lowered to 3.8 by means of concentrated hydrochloric acid. The volume is adjusted exactly to 10 liters by means of demineralized water, and with vigorous stirring 10 liters of ethanol are added. This is left to stand 48 hours. The supernatant liquor is siphoned off and pooled with the other supernatant liquor obtained above. The precipitate can be recovered, washed with ethanol, ground, dried under vacuum.

230 grams of product having the following characteristics are obtained:
USP titer=52 uI/mg
Yin and Wessler titer=225 uI/mg
Average molecular weight=4000 to 5000 daltons
The supernatant liquors are pooled together.

The supernatant liquor is adjusted at pH7 with NaOH 5N. 10 liters of ethanol are added. This is left to stand 48 hours. The supernatant liquor is siphoned off and eliminated. The precipitate is recovered, washed with ethanol, ground, dried under vacuum. 120 g of oligosaccharides are obtained. This product IC 86 1536 has the following characterstics:

Molecular weight: $\leq 2.500$
USP units: 5 $\mu$/mg
Yin and Wessler titer: about 70 $\mu$/mg
HPLC: according to the profile on the FIGURE Said FIGURE represents the HPLC curves when studying the molecular weight distribution average of the soluble fractions recovered, under the following conditions:

column TSK 2000SW VII
solvent $Na_2SO_4$ 0.5M
rate 1 ml/min.
detection: UV 205 nm
GPC analysis conditions: number of slices 110, slice width: 0.05 min, base line 4000 min to 14000 min, slicing 5000 min to 10500 min, reference peak time 0.00 min window 10%.

By gel filtrating IC 86 1536 according to the usual techniques, an hexasaccharidic composition IC 86 1583 is obtained devoid of anticoagulant activity with the following characteristics:

Molecular weight $\leq 2000$
USP units: 0
Anti-Xa Y and W: about 30 $\mu$/mg
said product inhibits neoangiogenesis when associated with corticoids.

EXAMPLE 2

Activity on the neoangiogenisis of compositions IC 86 1536 and IC 86 1583.

The trials in vitro concerning anti angiogenisis are carried out on a chicken embryo chorioallantoic membrane 6 days old in culture in petri dishes.

Pellets are formed by mixing 5 $\mu$g of hydrocortisone with 10 $\mu$l of methylcellulose, compositions IC 86 1536 and IC 86 1583 are added in amounts varying from 5 $\mu$g to 100 $\mu$g. The pellets obtained are dried and placed on the chorioallantoic membrane to which they adhere. For each test 4 eggs are used.

After 48 hours of incubation, avascular zones are found and an important drop in the vascular zones can be seen. These results are reached in a remarkable way using only 6 $\mu$g of the tested products.

EXAMPLE 3

Action of hexasaccharidic composition IC 1583 on a B16 mouse melanoma.

Tests carried out on C57 BL/6 mice carrying B16 melanomas.

The treatment carried out during a period of 15 days, administered by a sub-cutaneous injection twice a day to each mouse of 0.15 mg of the hexasaccharide composition of acetate of cortisone in varying doses reduced during the treatment from 250 mg/kg/j to 40–50 mg/kg/j. At the end of the 15 day period the growth of the tumours has ceased. A regression of the tumours is advantageously observed.

EXAMPLE 4

Use of the soluble oligosaccharides to obtain oligosaccharides with affinity for acidic or basic fibroblast growth factor (aFGF and bFGF respectively) An example is given of the preparation of oligosaccharides with affinity for aFGF.

An aFGF-Sepharose matrix, consisting of aFGF covalently linked to Sepharose, was prepared using bovine brain aFGF and packed into a column. An overloading amount of hexasaccharidic composition IC 86 1583 was applied to the column, and, after extensive washing, bound oligosaccharides were eluted by increasing the ionic strength. The hexasaccharidic composition IC 86 1583 recovered were found to be practically homogeneous by ion-exchange HPLC.

We claim:

1. An oligosaccharide fraction of the heparin chain which has antithrombotic activity in vivo (as measured by the (Yin-Wessler test) lower than that of heparin, which oligosaccharidic fraction (1) is soluble in a 50/50 v/v water-alcohol 0.5% NaCl pH 3.8 mixture, (2) comprises oligosaccharides, the majority of which are between 2 and 14 saccharide units in length and which have at the reducing end a 2,5-anhydrommano unit, (3) has essentially no anticoagulant activity (as determined by the U.S.P. method), (4) has anti-Xa activity less than that of heparin, and (5) has an HPLC profile comprising a molecular weight average of about 2,430, a number average of about 1,980, and a peak molecular weight of about 1,850.

2. The oligosaccharide fraction of claim 1, wherein the 2,5-anhydromanno unit at the reducing end of a majority of the oligosaccharides is 2,5-anhydromannitol.

3. The oligosaccharide fraction of claim 1, wherein the majority of oligosaccharides are between 6 and 8 saccharide units in length.

4. The oligosaccharide fraction of claim 3, wherein the majority of oligosaccharides are 6 saccharide units in length.

5. An oligosaccharide fraction of the heparin chain, which has an antithrombotic activity in vivo (as measured by the Yin-Wessler test) lower than that of heparin, and which is soluble in a 50/50 v/v water-alcohol 0.5% NaCl pH 3.8 mixture, obtained in a process comprising, subjecting compositions formed from a majority of mucopolysaccharide chains having a molecular weight (MW) of about 1800 to 8000 daltons and a ratio of the Yin-Wessler/USP titers higher than that of heparin, to at least one fractionation step with a mixture of 50/50 (v/v) of (1) water containing about 0.5% of an organic salt and and (2) an organic solvent, in order to separate from said composition mucopolysaccharide chains having a MW lower than about 2000 and mucopolysaccharide chains having a sulfate content lower than the sulfate average of the compositions, and recovering the oligosaccharidic fraction from the 50/50 (v/v) water-solvent mixture by alcohol precipitation.

6. A process for preparing the oligosaccharide fraction of claim 1, comprising subjecting compositions formed from a majority of mucopolysaccharide chains having a molecular weight (MW) of about 1800 to 8000 daltons, and a ratio of the Yin-Wessler/USP titers higher than that of heparin, to at least one fractionation step with a mixture of 50/50 (v/v) of (1) water containing about 0.5% of an organic salt and (2) an organic solvent, in order to separate from said composition mucopolysaccharide chains having a (v/v) lower than about 200 and mucopolysaccharide chains having a sulfate content lower than the sulfate average of the compositions, and recovering the oligosaccharidic fraction from the 50/50 (v/v) water-solvent mixture by alcohol precipitation.

7. The process according to claim 6, which additionally comprises fractionating the oligosaccharide fractions soluble in the 50/50 (v/v) water-alcohol mixture according to their molecular weight by gel filtration or ion exchange chromatography and recovering the oligosaccharidic fractions obtained.

8. A process for obtaining oligosaccharides with affinity for fibioblast growth factors, comprising contacting the oligosaccharide fraction of claim 1 with fibroblast growth factor bound to a matrix packed into a column, washing the column to remove non-bound oligosaccharides and eluting the bound oligosaccharides by washing the column matrix with a series of elution buffers of increasing ionic strength, thereby recovering the oligosaccharides with affinity for fibroblast growth factors.

9. A process for obtaining oligosaccharides with affinity for fibioblast growth factors, comprising contacting the oligosaccharide fraction of claim 2 with fibroblast growth factor bound to a matrix packed into a column, washing the column to remove non-bound oligosaccharides and eluting the bound oligosaccharides by washing the column matrix with a series of elution buffers of increasing ionic strength, thereby recovering the oligosaccharides with affinity for fibroblast growth factors.

10. A process for obtaining oligosaccharides with affinity for fibioblast growth factors, comprising contacting the oligosaccharide fraction of claim 3 with fibroblast growth factor bound to a matrix packed into a column, washing the column to remove non-bound oligosaccharides and eluting the bound oligosaccharides by washing the column matrix with a series of elution buffers of increasing ionic strength, thereby recovering the oligosaccharides with affinity for fibroblast growth factors.

11. A process for obtaining oligosaccharides with affinity for fibioblast growth factors, comprising contacting the oligosaccharide fraction of claim 4 with fibroblast growth factor bound to a matrix packed into a column, washing the column to remove non-bound oligosaccharides and eluting the bound oligosaccharides by washing the column matrix with a series of elution buffers of increasing ionic strength, thereby recovering the oligosaccharides with affinity for fibroblast growth factors.

12. A process for obtaining oligosaccharides with affinity for fibioblast growth factors, comprising contacting the oligosaccharide fraction of claim 5 with fibroblast growth factor bound to a matrix packed into a column, washing the column to remove non-bound oligosaccharides and eluting the bound oligosaccharides by washing the column matrix with a series of elution buffers of increasing ionic strength, thereby recovering the oligosaccharides with affinity for fibroblast growth factors.

* * * * *